(12) United States Patent
Pflanz et al.

(10) Patent No.: US 8,697,436 B2
(45) Date of Patent: Apr. 15, 2014

(54) SINGLE USE, DISPOSABLE DIAPHRAGM VALVE IN WHICH THE VALVE BODY AND SEALING MEMBRANE ARE WELDED TO ONE ANOTHER

(75) Inventors: Karl Pflanz, Reinhausen (DE); Andreas Graus, Nörten-Hardenberg (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 0 days.

(21) Appl. No.: 13/143,303

(22) PCT Filed: Dec. 2, 2009

(86) PCT No.: PCT/EP2009/008574
§ 371 (c)(1),
(2), (4) Date: Sep. 22, 2011

(87) PCT Pub. No.: WO2010/078891
PCT Pub. Date: Jul. 15, 2010

(65) Prior Publication Data
US 2012/0015394 A1    Jan. 19, 2012

(30) Foreign Application Priority Data
Jan. 12, 2009  (DE) .......................... 10 2009 004 667

(51) Int. Cl.
| C12M 1/00 | (2006.01) |
| C12M 3/00 | (2006.01) |
| C12M 1/22 | (2006.01) |
| B01L 3/00 | (2006.01) |

(52) U.S. Cl.
CPC ............... *C12M 23/10* (2013.01); *B01L 3/508* (2013.01)
USPC ........................... 435/289.1; 435/29; 435/243

(58) Field of Classification Search
CPC . C12Q 11/04; B01L 3/508; B01L 2200/0689; B01L 2300/0851; G01N 2001/0281; C12M 27/02; C12M 35/04; C12M 21/04; C12M 29/10; C12M 23/14

USPC .............................. 435/29, 243, 283.1, 289.1
See application file for complete search history.

(56) References Cited

U.S. PATENT DOCUMENTS 4,668,633 A    5/1987  Walton
(Continued)

FOREIGN PATENT DOCUMENTS

| DE | 4220560 C1 | 9/1993 |
| DE | 19823993 A1 | 12/1999 |

(Continued)

OTHER PUBLICATIONS

Machine translation of DE 19823993 A1. Translated on Feb. 19, 2013.*

(Continued)

*Primary Examiner* — Michael Hobbs
(74) *Attorney, Agent, or Firm* — Cohen & Hildebrand, PLLC

(57) ABSTRACT

The invention relates to a transfer unit for receiving in particular a porous disc-shaped medium from a first treatment device, having an upper part, wherein the upper part comprises a fixing edge that can be connected to an edge of the medium for removing the medium from the first treatment device, wherein the upper part comprises an opening closed by a removable cover, by means of which successive treatments in a further treatment device can be performed. The invention further relates to a method wherein an upper part of a transfer unit is placed on a disc-shaped medium disposed in a first lower part of a first treatment device and exposed to the liquid sample and is connected to an edge of the medium, wherein the upper part is lifted off from the first lower part with the disc-shaped medium connected thereto, and is placed on a further lower part of a corresponding treatment device, and is further processed through an opening in the upper part.

13 Claims, 3 Drawing Sheets

(56) References Cited

U.S. PATENT DOCUMENTS

Figure 1:
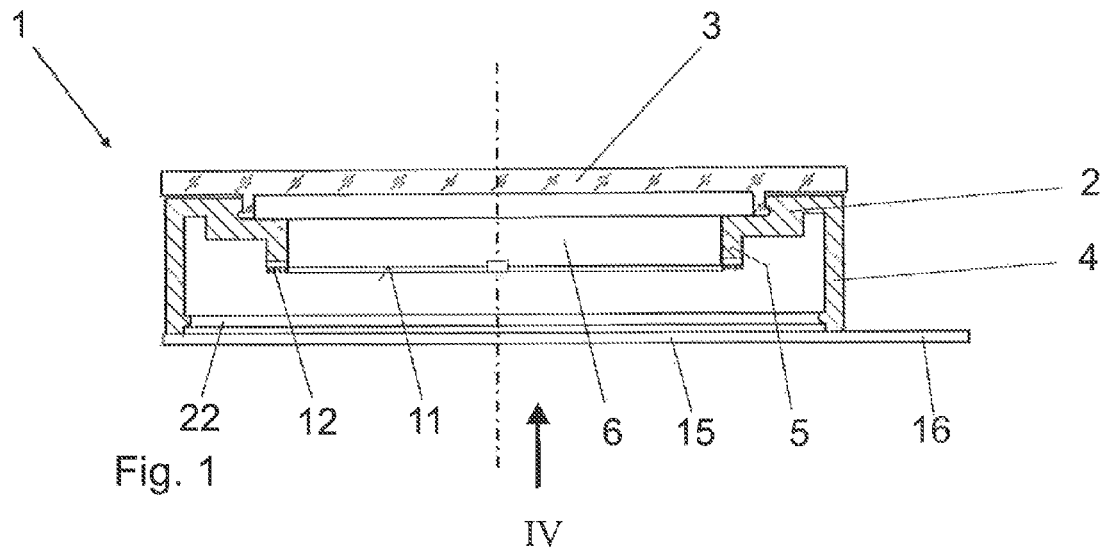

| | | |
|---|---|---|
| 2002/0096468 A1 | 7/2002 | Zuk |
| 2010/0028933 A1 | 2/2010 | Pflanz |
| 2010/0086959 A1 | 4/2010 | Pflanz |

FOREIGN PATENT DOCUMENTS

| | | |
|---|---|---|
| DE | 202004001703 | 4/2004 |
| DE | 102005008220 B3 | 8/2006 |
| DE | 102007014082 A1 | 9/2008 |
| DE | 102008005968 A1 | 9/2008 |
| WO | 2008113443 A1 | 9/2008 |
| WO | 2008113444 A1 | 9/2008 |

OTHER PUBLICATIONS

Machine Translation of DE 10 2008 005 968 A1. Translated on Sep. 5, 2013.*

International Search Report dated May 6, 2010.

* cited by examiner

SINGLE USE, DISPOSABLE DIAPHRAGM VALVE IN WHICH THE VALVE BODY AND SEALING MEMBRANE ARE WELDED TO ONE ANOTHER

This is an application filed under 35 USC §371 of PCT/EP2009/008574 and claiming priority under DE 10 2009 004667.4 filed on Dec. 1, 2009.

BACKGROUND OF THE INVENTION (1) Field of the Invention

The invention relates to a transfer unit for receiving in particular a porous, disk-shaped medium from a first treatment device, which has at least one upper part, the upper part having a fixing edge, which can be connected to an edge of the medium for the removal of the medium from the first treatment device.

Furthermore, the invention relates to a method for the microbiological examination and/or treatment of liquid samples, in which an upper part of a transfer unit is placed on a disk-shaped medium, which is arranged in a first lower part of a first treatment device and exposed to the liquid sample, such that a fixing edge arranged in the upper part is connected to an edge of the medium, and wherein the upper part with the connected disk-shaped medium is lifted from the first lower part and placed onto a further lower part of a further treatment device corresponding to the upper part.

(2) Description of Related Art

In the analysis of liquids and gases various treatment methods have become established which use porous media, such as filters and membranes. For example, the filtration method for the depletion and concentration of dissolved or particulate components has become established. This concentration is generally necessary, since the concentrations of the impurities are too low to carry out direct evaluations. The filtration methods are used as an initial stage for further analytical methods, such as optical evaluations, as well as for further physical and chemical reactions for signal amplification.

From DE 10 2008 005 968 A1 a nutrient medium unit and a method for receiving a filter of a filtration device are known. The nutrient medium unit is here composed of a lid, which forms the actual transfer unit, and of a lower part filled with nutrient medium. The upper part is embodied as a lid and has a fixing edge, which can be connected to an edge of the filter via an adhesive bond for the removal of the filter or medium from the filtration or treatment device.

Furthermore, from DE 10 2008 005 968 A1 a method is known for the microbiological analysis of liquid samples, in which an upper part or lid of a nutrient medium unit is placed onto a filter, embodied as a membrane filter with a fixing edge, arranged in a lower part of a filter device or treatment device. The fixing edge of the lid is in this case connected to an edge of the filter via an adhesive layer. Subsequently, the upper part with the filter is lifted from a filter support of the lower part of the filter device and placed on a surface of a nutrient medium arranged in the lower part of a nutrient medium unit, with the upper part or the lid covering the lower part, which is embodied in a dish-shaped manner.

However, the disadvantage with the known nutrient medium unit and the method, which have proven useful for classic microbiological membrane applications, in which only colonies that have formed are visually evaluated, is that no further filtration or aftertreatment can be directly added immediately after the transfer without detaching the filter again from the lid or the transfer unit. In the known method, in which the filter fixing in contact with liquid, can become detached again by itself at a later time, a further later treatment step is necessary in order to pick up the detached filter membrane again and move it to other treatments or to insert it into other units.

These disadvantages are important particularly in the case of applications which do not correspond to the classic growth of retained germs on agar, but use modern molecular-biological labeling and detection methods, regardless of whether these are methods which require a preincubation or are directly examined by labeling or intensification methods.

BRIEF SUMMARY OF THE INVENTION

The object of the present invention is therefore to provide a device and a method with which it is possible to introduce in particular a porous, disk-shaped medium into a further treatment station easily and cost-effectively without complicated equipment and without the use of an additional aid.

With regard to the device, the object is attained in connection with a transfer unit for receiving a porous, disk-shaved medium from a first treatment device that includes an upper part has having an opening that can be closed with a removable lid, via which opening a subsequent treatment can be carried out in a further treatment device.

The surface of the disk-shaped medium is thus also accessible for further processing steps due to the removable lid. Accessibility from bath sides is particularly important for porous media, since in this case treatment is possible from above as well as from below the porous medium. However, impermeable membranes and films can also be transferred with this transfer unit.

According to a preferred embodiment of the invention, the upper part forms a peripheral contour that corresponds to the treatment devices, which can be placed into the opening of the upper part, and/or that corresponds to treatment devices onto which the upper part can be placed. An aftertreatment of the medium in different treatment devices is thus rendered possible in a simple and cost-effective manner.

According to a further preferred embodiment of the invention, the fixing edge of the upper part has an adhesive layer of a suitable adhesive. However, in principle it is also possible for the adhesive layer of a suitable adhesive to be arranged on the edge of the disk-shaped medium.

Due to the adhesive layer the disk-shaped medium adheres to the upper part and can be easily and simply removed from the treatment device and placed in another treatment device. The disk-shaped medium, which is matched to the provided treatment device, is usually embodied in a rotationally symmetrical manner, but can also have a rectangular or another polygonal structure, as well as geometrically irregular formats. In its peripheral contour, the corresponding transfer unit or the upper part is functionally matched to the contour or structure of the disk-shaped medium such that it produces an adhesive contact only in the region that is not used for further analysis.

The adhesive layer is made of a PSA dispersion adhesive or of acrylate-copolymer microbeads. This means that even wet filters can be adequately bonded to and removed again from the fixing edge of the lid. Suitable pressure-sensitive adhesives are known to one skilled in the art, for example, as microbead-based acrylate adhesives.

According to a further embodiment of the invention, the adhesive can be sterilized by means of conventional methods. The adhesive is preferably DNA-free and protein-free and does not exhibit any non-specific reactions with antibody-based reagents. In particular, adhesives can be used which have only slight autofluorescence and do not bond non-specifically with corresponding coloring and labeling reagents. This applies in particular to wavelength ranges of 400 to 800 nm commonly used in evaluation. Adhesives can also be used that do not have any antibiotic or fungicidal properties.

According to a further preferred embodiment of the invention, the disk-shaped medium is embodied as a filter and the first treatment device is embodied as a filter device. The filter embodied, for example, as a porous membrane filter can in this case be easily removed from the filter device and conveyed to a further treatment device.

According to a further preferred embodiment of the invention, the fixing edge is formed by a free end face of an inner wall arranged on an upper part inner surface facing towards a lower part of the treatment device. In this case, the, for example, annular inner wall on the one hand ensures the necessary spacing between the disk-shaped medium and the upper part, and on the other hand its diameter, in relation to the diameter of the medium, is chosen such that only the outer edge of the medium comes into contact with the adhesive layer of the adhesive bond, the edge being arranged outside the used area of the medium.

According to a further preferred embodiment, the fixing edge is formed by the outer wall of an inner wall arranged on an upper part inner surface facing towards a lower part of the treatment device, the inner wall being embodied, for example, as an annular clamping part, which can be clamped with the medium via a reinforcing edge of the medium. An attachment of this type by an annular clamping part is disclosed by DE 10 2007 014 082 A1.

According to a further preferred embodiment of the invention, on its outer wall the upper part has a positioning aid with respect to the treatment device or the lower part of the treatment device or an analysis device. This renders possible in a repeatable manner a reproducible, location-specific treatment and evaluation, which can also be carried out automatically.

The positioning aid is preferably embodied as a mechanical shaping, which permits a reproducible positioning between the upper part and the treatment device with corresponding shaping and thus also between the medium adhering to the upper part and the treatment device. In principle other markings are also possible, e.g. printing or etching in the region of the outer wall of the upper part.

According to a further preferred embodiment of the invention, the lid that can be inserted into the opening of the upper part is embodied in a transparent manner. When using certain optical evaluation methods, this renders possible an evaluation with the lid closed.

According to a further preferred embodiment of the invention the upper part has a receiving projection delimited by its outer wall, which receiving projection can be placed onto a corresponding lower part in a sealing manner and wherein the lid-side opening can likewise be sealed by an insertable lid.

In many cases, the aftertreatment steps are carried out on an aqueous basis, and a tight connection permits the removal of excess volume, whether by vacuum or by pressure.

According to a further preferred embodiment of the invention, a lower part embodied in a disk-shaped manner is provided as part of the transfer unit, the part having a nutrient medium, on the upper surface of which facing towards the upper part the disk-shaped medium adhering to the lid can be placed.

The transfer unit composed of the upper part with lid and of the lower part can in this case be used as a nutrient medium unit for receiving the disk-shaped medium, for storing it and for its aftertreatment.

As regards the method, the further object is attained in conjunction with the preamble of claim 15 in that at least one further examination and/or treatment of the sample constituents adhering to the disk-shaped medium takes place through an opening in the upper part.

A time-consuming detachment of the disk-shaped medium from the upper part can be omitted due to the aftertreatment through an opening in the upper part. This means that aftertreatments with different treatment devices are substantially simplified and improved. A lid inserted into the opening in the upper part, closing the opening, can be removed before further examination and/or treatment of the sample constituents adhering to the disk-shaped medium.

According to a further preferred embodiment of the invention, before the first use of the upper part, a cover sealing the upper part in a sterile manner on its side facing away from the lid opening is removed.

The transfer unit, composed of the upper part with inserted lid, closed at the bottom by a sealing cover, can thus be supplied in a sterile packaging wrapper. Before the first use, the transfer unit then needs merely to be unpacked and the sealing cover, which is embodied, for example, as an adhering film, removed.

Instead of the cover sealing the transfer unit, the transfer unit can also be supplied with a dish-shaped lower part.

The lid of the upper part here serves as a closure in order on the one hand to ensure sterility and on the other hand, for example, to protect the sample from external effects.

The result is a simple and cost-effective manipulation of the medium with the applied sample.

According to a further embodiment of the invention, after filtration in the first treatment device as well as after optionally further treatment steps for signal amplification, the medium embodied as a filter disk, e.g. a membrane, is placed with the transfer unit on a stable support disk, which likewise has an adhesive layer of a suitable adhesive, and in a subsequent step is inserted with the support disk into an automatic evaluation unit for an automatic evaluation.

The surficial fixing to the support disk ensures that the evaluation process takes place over a defined focusing plane. The evaluation can in this case take place either directly on the membrane surface or through the highly transparent support disk.

This makes it possible for the disk-shaped medium to be evaluated with electronic evaluation units, such as, for example, laser scanners.

Thus for a microbiological analysis, for example, pore sizes in the microfiltration range must be used in order to be able to reliably retain the microorganisms. Since the filtration flows decrease proportionally to the thickness of the medium or filter and to decreasing pore diameter, the filtration media are thin. For disk-shaped porous media, thicknesses of approx. 100 to 200 μm are typical. Filtration media of this type cannot be used without support in evaluation units with laser-scanner technology.

Using the transfer unit according to the invention, a medium embodied as a filter disk can be applied to a stable support disk after filtration and the necessary treatment steps have been carried out.

Further features of the invention are given in the following detailed description and the attached drawings, which illustrate preferred embodiments of the invention by way of example.

BRIEF DESCRIPTION OF THE SEVERAL VIEWS OF THE DRAWING(S)

Figure 2:
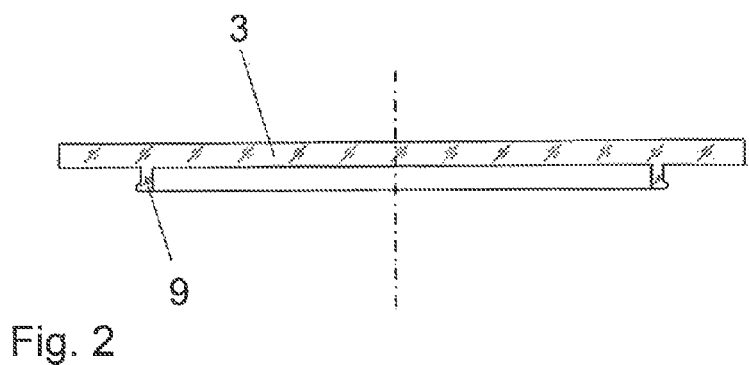
Figure 3:
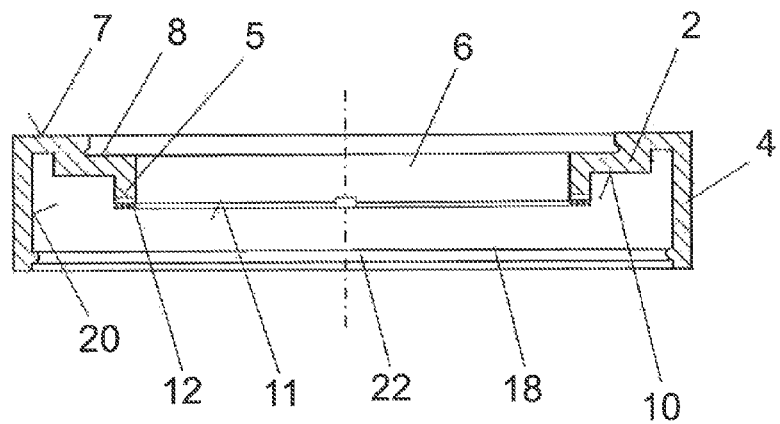
Figure 4:
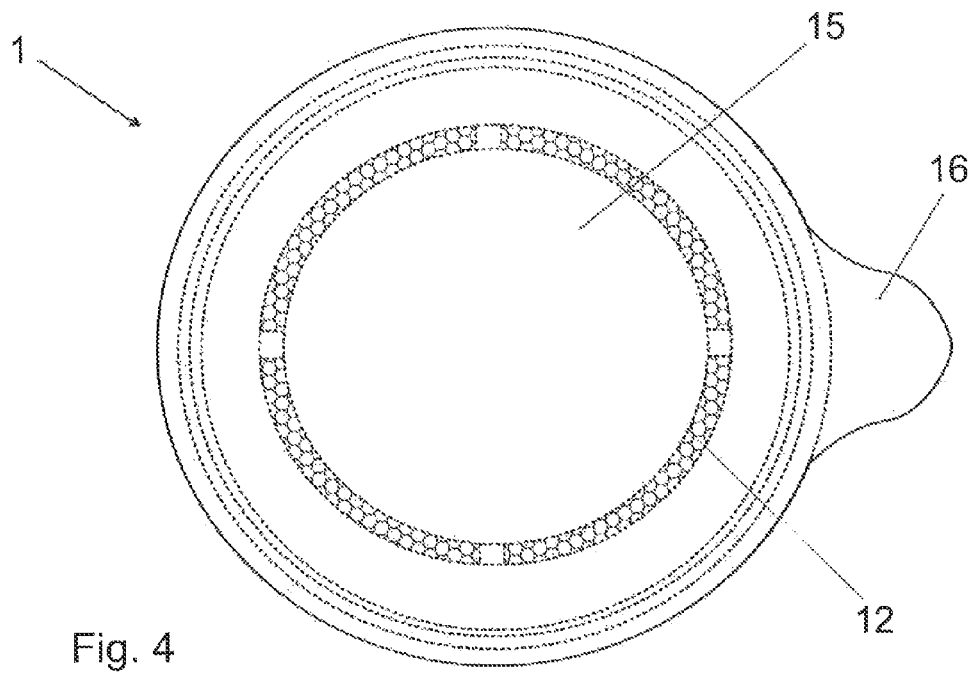
Figure 5:
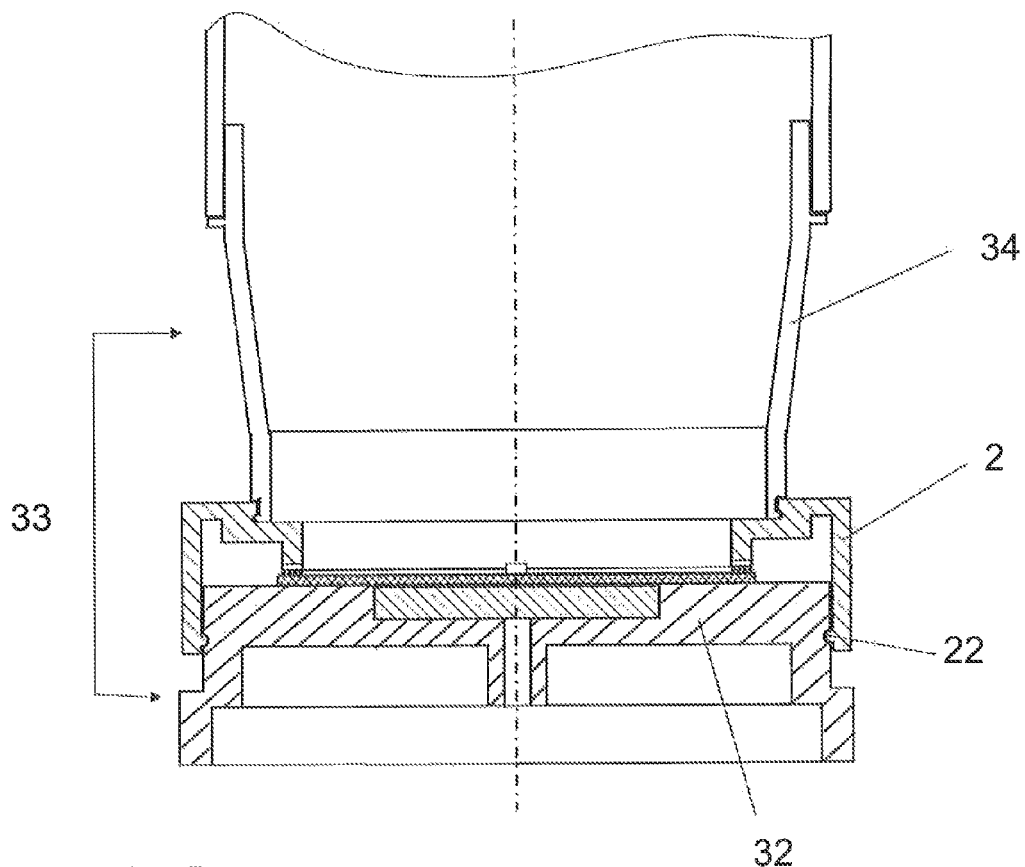
Figure 6:
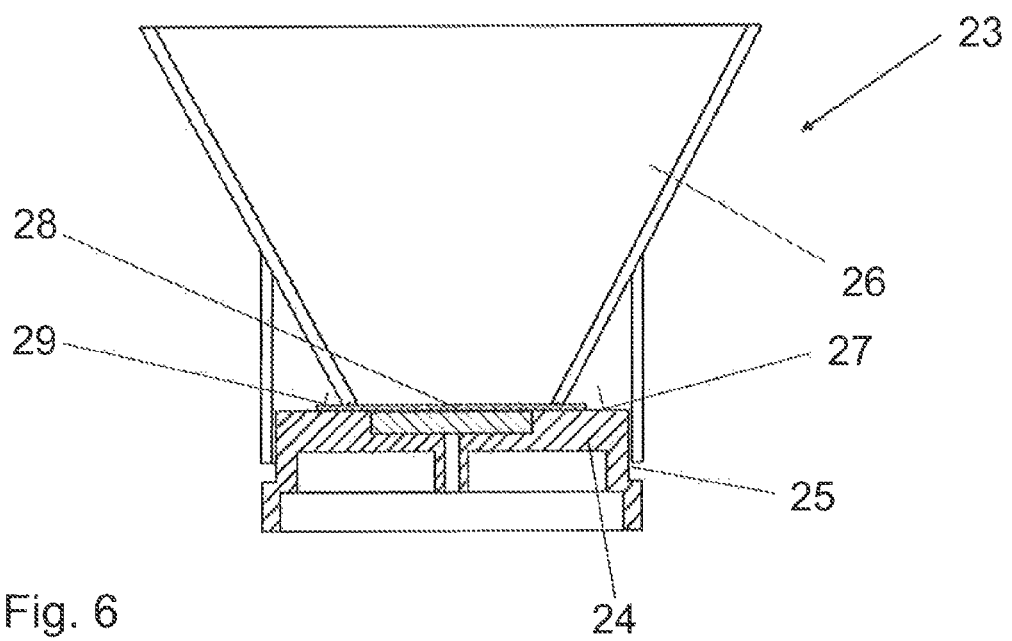
Figure 7:
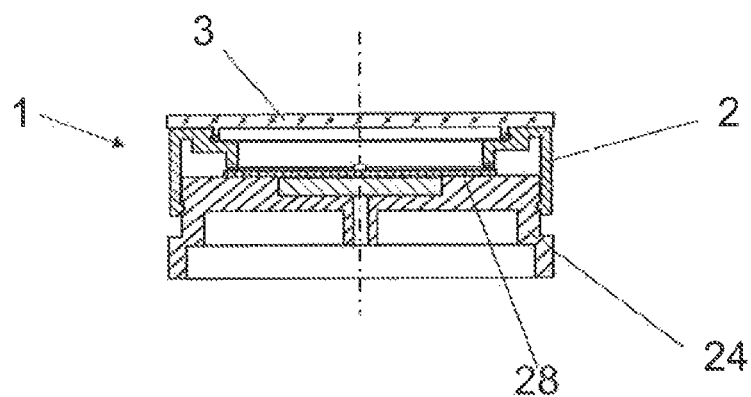

The drawings show:

FIG. 1: cross-sectional side view of a transfer unit, composed of an upper part with lid and a sterile-sealing cover;

FIG. 2: A cross-sectional side view of the lid from FIG. 1;

FIG. 3: A cross-sectional side view of the upper part from FIG. 1;

FIG. 4: A bottom view of the transfer unit from FIG. 1 from direction IV;

FIG. 5: A cross-sectional side view of a transfer unit inserted in a treatment device for aftertreatment;

FIG. 6: A cross-sectional view of a treatment device embodied as a filtration device;

FIG. 7: A cross-sectional side view of an upper part of a transfer unit with lid placed on the lower part with a disk-shaped medium from FIG. 6 and FIG. 8: A cross-sectional side view of the upper part from FIG. 7 with a disk shaped medium placed on a lower part of a transfer unit.

DETAILED DESCRIPTION OF THE INVENTION

A transfer unit 1 is composed essentially of an upper part 2 and a lid 3. The upper part 2 forms a peripheral contour with an outer wall 4 and a parallel-oriented inner wall 5 which encloses an opening 6 in the upper part 2. On its top side 7, the upper part 2 has a shoulder 8, which encloses the opening 6 and accommodates the lid 3 with a projection 9. The upper part 2 has the inner wall 5 on its upper part inner surface 10 facing away from the top side 7, the free end of which inner wall 5 forms a fixing edge 11 with its end face. In the exemplary embodiments the fixing edge 11 has an adhesive layer 12 of a suitable adhesive. The adhesive layer 12 is composed, for example, of a PSA dispersion adhesive or of acrylate-copolymer microbeads. The removable lid 3 can be placed with its projection 9 in the shoulder 8 into the upper part 2 in a sealing manner. The sealing insertability can be ensured, for example, by conical bevels or by peripheral clamping depending on the material of the lid 3 or upper part 2. The lid 3 is made of a transparent plastic.

According to the exemplary embodiment of FIGS. 1 and 4, the upper part 2 has a sealing cover 15 on its free end of the outer wall 4, which sealing cover can be pulled off the upper part 2 or the outer wall 4 using a tab 16.

Figure 8:
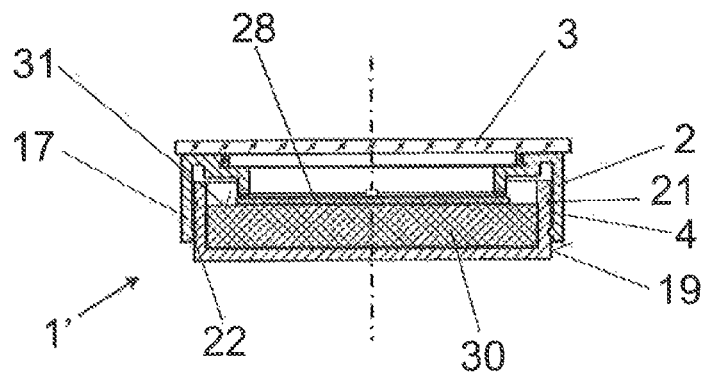

Instead of the cover 15, the transfer unit 1' also according to the exemplary embodiment of FIG. 8 can also have a lower part 17, onto which the upper part 2 can be placed with a receiving projection 18 laterally delimited by its outer wall 4. An outer wall 19 of the lower part 17 can then bear against the inner side 20 of the outer wall 4.

A first treatment device 23 known per se, which is embodied according to FIG. 6 as a filtration device, is composed of a lower part 24 with a receiving projection 25, on which a funnel-shaped attachment 26 can be placed. A disk-shaped medium 28, which is embodied, for example, as a porous filter membrane, is arranged between the attachment 26 and a filter support surface 27 of the lower part 24.

After a filtration process, the attachment 26 can be removed from the lower part 24 and the upper part 2 of the transfer unit 1, 1' can be placed with inserted lid onto the lower part 24 instead of the attachment 2.6. The upper part 2 is in this case placed with its fixing edge 11 onto an edge 29 of the disk-shaped medium 28 such that the disk-shaped medium 28 adheres to the adhesive layer 12 of the fixing edge 11 and can be accommodated by the lower part 24. The transfer unit 1, 1' or the upper part 2 can now be placed onto the lower part 17 that is embodied in a dish-shaped manner, into which a nutrient medium 30 has been introduced, with the disk-shaped medium 28 bearing against a top side 31 of the nutrient medium 30. After removal of the lid 3 from the upper part 2, further treatment steps can be carried out through the opening 6. The transfer unit 1, 1' or the upper part 2 can also be placed with the disk-shaped medium 28 onto a lower part 32 of a further treatment device 33.

According to FIG. 5, after removal of the lid 3, a funnel attachment 34 of the further treatment device 33 or another treatment device (not shown) can be inserted into the opening 6 in a sealing manner. The sealing insertability of the upper part 2 on the lower part 32 and of the funnel attachment 34 on the upper part 2 can be ensured, for example, by conical bevels or by peripheral clamping depending on the material of lower part 32, upper part 2 and funnel attachment 34. According to FIG. 5, a peripheral sealing bead 22 can engage into a corresponding, likewise peripheral recess of the lower part 32.

The invention claimed is:

1. A transfer unit (1, 1') for receiving a porous, disk-shaped medium (28) from a first treatment device (23), comprising
at least one upper part (2), the upper part (2) having a fixing edge (11), connected to an edge of the medium (28) for the removal of the medium (28) from the first treatment device (23) and a removable lid (3),
wherein
the upper part (2) has an opening (6) closeable with the removable lid (3), via which opening a subsequent treatment is carried out in a further treatment device (33) and the fixing edge (11) is connected along a plurality of segments to the edge of the medium (28) via a circular adhesive bond; wherein the upper part (2) forms a peripheral contour with an outer wall (4) and a parallel-oriented inner wall (5) closed off by a shoulder (8) extending therebetween; wherein the outer wall (4), the inner wall (5) and the shoulder (8) together form a J-shape cross-section.

2. The transfer unit according to claim 1, wherein the upper part (2) forms a peripheral contour, which corresponds to the treatment devices (23, 33), which is placed into the opening (6) of the upper part (2) and/or which corresponds to treatment devices (23, 33), onto which the upper part (2) is placed.

3. The transfer unit according to claim 1, wherein the fixing edge (11) of the upper part (2) has an adhesive layer (12).

4. The transfer unit according to claim 1, wherein an edge (29) of the disk-shaped medium (28) has an adhesive layer (12).

5. The transfer unit according to claim 3, wherein an adhesive of the adhesive layer is applied in a sterilizable manner.

6. The transfer unit according to claim 5, wherein the adhesive is applied in a DNA-free and protein-free manner and does not exhibit any non-specific reactions with antibody-based reagents.

7. The transfer unit according to claim 1, wherein the disk-shaped medium (28) is embodied as a filter and the first treatment device (23) is embodied as a filter device.

8. The transfer unit according to claim 1, wherein the fixing edge (11) is formed by a free end face of an inner wall (5) arranged on an upper part inner surface (10) facing towards a lower part (17) of the treatment device (23).

9. The transfer unit according to claim 1, wherein the upper part (2) includes an outer wall (4) and wherein the upper part (2) has a positioning aid with respect to the treatment device (23, 33).

10. The transfer unit according to claim 1, wherein the lid (3) is insertable into the opening (6) of the upper part (2) and is transparent.

11. The transfer unit according to claim 1, wherein the upper part (2) has a receiving projection (18) delimited by an outer wall (4), which receiving projection is placed onto a corresponding lower part (17) and the lid (3) is inserted into the opening (6) seals the opening (6).

12. The transfer unit according to claim 1, wherein a dish-shaped lower part (17) is provided as part of the transfer unit (1') and contains a nutrient medium (30) having a top side (31) facing towards the upper part (2), onto which the disk-shaped medium (28) adhering to the lid (3) is placed.

13. The transfer unit according to claim 1, wherein free ends of the outer wall (4) and the inner wall (5) are oriented in the same direction, and the free end of the inner wall (5) forms the fixing edge (11).

* * * * *

UNITED STATES PATENT AND TRADEMARK OFFICE
CERTIFICATE OF CORRECTION

| | | |
|---|---|---|
| PATENT NO. | : 8,697,436 B2 | Page 1 of 1 |
| APPLICATION NO. | : 13/143303 | |
| DATED | : April 15, 2014 | |
| INVENTOR(S) | : Pflanz et al. | |

It is certified that error appears in the above-identified patent and that said Letters Patent is hereby corrected as shown below:

On the Title Page: Item (54) and in the Specification: Column 1, Lines 1-4, Title should read:
--TRANSFER UNIT AND METHOD FOR RECEIVING A MEDIUM FROM A PROCESSING DEVICE--

Signed and Sealed this
Twelfth Day of August, 2014

Michelle K. Lee
*Deputy Director of the United States Patent and Trademark Office*